United States Patent [19]

Oshima et al.

[11] Patent Number: 4,717,464

[45] Date of Patent: Jan. 5, 1988

[54] OXYGEN SENSOR

[75] Inventors: Norio Oshima, Nagoya; Takao Murase, Konan; Shuichiro Oki, Aichi, all of Japan

[73] Assignee: NGK Insulators, Ltd., Japan

[21] Appl. No.: 900,892

[22] Filed: Aug. 27, 1986

[30] Foreign Application Priority Data

Sep. 2, 1985 [JP] Japan .................... 60-133045[U]
Sep. 2, 1985 [JP] Japan .................... 60-133046[U]

[51] Int. Cl.⁴ ............................................ G01N 27/46
[52] U.S. Cl. ................................... 204/427; 204/428
[58] Field of Search .................... 204/1 S, 421–429

[56] References Cited

U.S. PATENT DOCUMENTS 4,040,930 8/1977 Dillon ............................. 204/429
4,116,797 9/1978 Akatsuka ........................ 204/428
4,247,380 1/1981 McIntyre ........................ 204/1 S
4,297,192 10/1981 Shinohara et al. .............. 204/428
4,323,440 4/1982 Akatsuka ........................ 204/428

Primary Examiner—T. Tung
Attorney, Agent, or Firm—Parkhurst & Oliff

[57] ABSTRACT

The invention provides an oxygen sensor for detecting oxygen concentration in exhaust gas from an internal combustion engine. The oxygen sensor comprises a closed-end tube of solid electrolyte having an inside reference electrode communicating with the atmosphere and an outside measuring electrode which is exposed to the exhaust gas, a housing to support the tube, a metallic sleeve fixed to the housing to isolate the reference electrode from the exhaust gas, while atmospheric air is allowed to enter into the tube through air passages on the metallic sleeve. The passages are protected by a filter securely fixed to the metallic sleeve, pressed by an elastic member thereagainst, whereby water or mud are prevented from entering into the tube while the sensor is operating.

6 Claims, 7 Drawing Figures

OXYGEN SENSOR

BACKGROUND OF THE INVENTION

1. Field of the Invention

The present invention relates to an oxygen sensor for detecting an oxygen concentration in an exhaust gas discharged from internal combustion engines, and more particularly, to a water-proof structure for the oxygen sensor wherein atmospheric pressure is used as a reference gas.

2. Related Art Statement

Heretofore, it has been known to detect oxygen concentration in the exhaust gas of internal combustion engines, such as automobile engines, etc., by using an oxygen ionic conductive solid electrolyte, according to the principle of oxygen concentration cell, to regulate an air-fuel ratio of the internal combustion engines. Oxygen sensors of this type utilize a tube with a closed end of a zirconia solid electrolyte provided on its inside and outside surfaces respectively with a porous platinum electrode, the inner electrode communicating with atmospheric air to form an electrode having a reference oxygen concentration, while the outer electrode, which functions as a measuring electrode, is exposed to the gas to be measured, i.e., exhaust gas. The communication with the atmosphere is achieved by providing, as an air passage, a clearance between a housing supporting the solid electrolyte tube and a metallic sleeve, or an aperture provided through the metallic sleeve or an electrode terminal for detecting oxygen concentration.

However, such conventional oxygen sensors generally have a drawback, when used in internal combustion engines, that water, brine, mud, etc. enter from the air passage, causing the solid electrolyte, under a high temperature condition, to break or the electrode can become corroded.

In order to solve the above-mentioned problem, an air passage provided on a metallic sleeve has been covered by a filter, as proposed in U.S. Pat. No. 4,116,797.

In this oxygen sensor, however, since the filter is only inserted into the air passage of the metallic sleeve, upon exposure of the oxygen sensor to a high temperature ambience in an internal combustion engine, the filter is prone to be detached due to a difference in thermal expansion between the filter and the metal, and in particular, the above problem occurs in the case where a heater member for heating the solid electrolyte is provided inside the solid electrolyte tube for the purpose of enabling the oxygen sensor to accurately detect oxygen concentration when internal combustion engines are first started.

Further, in such an oxygen sensor provided with a heater member inside, a lead wire for supplying power to the heater member, in addition to the electrode terminal for detecting oxygen concentration, must be inserted through the rubber grommet so that it is difficult to provide a filter in a limited, narrow area of the rubber grommet.

SUMMARY OF THE INVENTION

Accordingly, an object of the present invention is to provide an improved oxygen sensor having a solid electrolyte tube, the inside surface of which is provided with a reference electrode connected by an air passage with the atmosphere, while not permitting water or moisture to enter into the solid electrolyte tube.

A further object of the invention is to fix a filter to the entrance of the air passage leading to the reference electrode, securely with no fear of it coming off, while occupying a limited, narrow area, and thereby not interfering with insertion of the lead wire.

Other objects and advantages of the present invention will become apparent from the detailed descriptions that follow.

The above objects of the invention are attained by an improvement in an oxygen sensor comprising a solid electrolyte tube 1 with a closed end having an electrode on its inside and outside surfaces respectively, a housing 2 supporting said electrolyte tube and isolating the inside of the electrolyte tube hermetically from exhaust gas, while exposing said closed end protruding from the housing to the exhaust gas and a metallic sleeve 3 fixed to said housing, enclosing the opened end of said solid electrolyte tube and having an air passage 5 in the direction of an electrode terminal 4, which is characterized by further comprising a filter 6 covering said air passage 5 and a first elastic member 7 supporting said filter, said first elastic member 7 having a plurality of apertures 18 and an air groove 17 communicating with said apertures.

According to the above-described filter used in the present invention, the air passage can be covered watertightly, as it leads to the atmosphere, and by means of a metallic cover and a second elastic member, the filter can be held securely, so as not to readily come off. Further, the filter can be located without any restriction about its position, and a sufficient space for any lead wires to be inserted remains.

BRIEF DESCRIPTION OF THE DRAWINGS

With reference to the accompanying drawings.

DESCRIPTION OF THE PREFERRED EMBODIMENT

Figure 1:
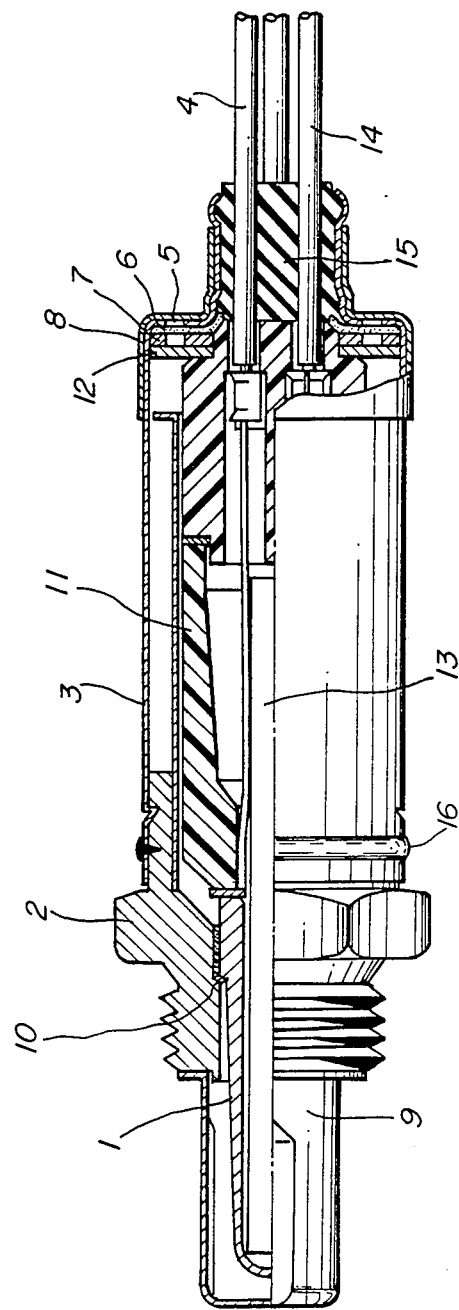
FIG. 1 is a partial sectional view illustrating an embodiment of the present invention.

The present invention will be explained by the embodiments with reference to the drawing hereinafter.

In FIG. 1, a solid electrolyte tube 1 is supported by a housing 2, sealed up with a metallic packing 10 in such a manner that the inside of the electrode is hermetically isolated from the gas to be measured. On one end of housing 2, a perforated metallic protective cover 9 is fixed to hedge off the outside peripheral surface of the closed end of solid electrolyte tube 1 from direct contact with the gas to be measured.

On the opened side of solid electrolyte tube 1, an electrode terminal 4 in contact with the reference electrode provided on the inside peripheral surface of solid electrolyte tube 1 and an electric insulation member 11 to press the electrode terminal 4 are sequentially joined.

A second elastic member 12, such as a coned disc spring or the like, presses both a filter 6, as explained hereinafter, and a first elastic member 7 having a plurality of apertures 18 therein (refer to FIG. 2), stacked on the filter 6. The metallic sleeve 3 is fixed on the other end of the aforesaid housing 2 by means of caulking and further is welded hermetically along its entire periphery alongside and outward of the caulked line, forming a welding trace 16.

Then, the metallic sleeve 3 has air passages 5 therein just under which is provided the filter 6 in contact with the inside surface of the sleeve 3. Into the solid electrolyte tube 1 is inserted a heater member 13 for heating the solid electrolyte, and then an electrode terminal 14 for supplying power to the heater member 13 extends alongside the aforesaid electrode terminal 4 in the direction of the air passages 5.

Moreover, the above-described metallic sleeve 3 extends farther beyond air passages forming a neck wherein a rubber grommet 15 with said electrode terminals 4 and 14 inserted therethrough is plugged and fixed watertightly. When this portion is exposed to a high temperature, the watertightness around the rubber grommet 15 may be reduced due to a difference in thermal expansion between the metallic sleeve 3 and the rubber grommet 15, so that the filter 6 is made to extend and attach tightly to the end surface of electric insulation member 11 at the bottom end of rubber grommet 15, thereby maintaining the watertightness.

The air passages 5 are covered by the filter 6 from the inside of the metallic sleeve 3. The filter 6 is further pressed against the inside surface of the metallic sleeve 3, by the first elastic member 7, by means of the second elastic member 12, which can be, for example, a coned disc spring.

Figure 2:
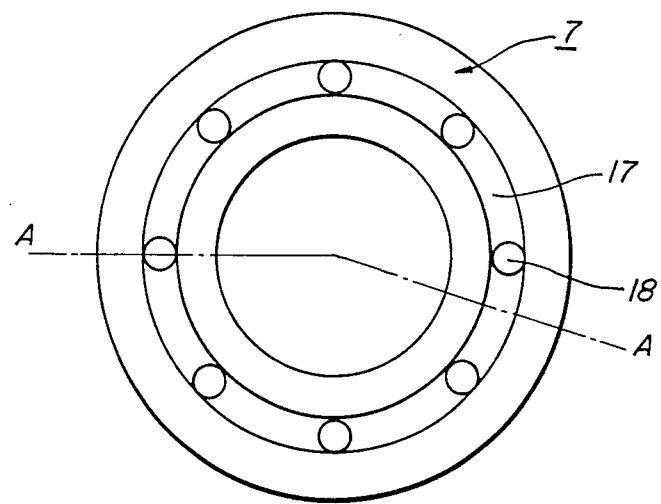
FIG. 2 is a plan view of an elastic member to be used in the embodiment of the present invention.
Figure 3:
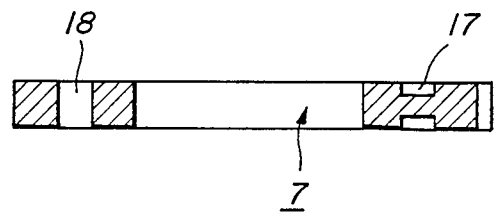
FIG. 3 is a sectional view along the line A—A of FIG. 2.

The first elastic member 7 is provided with an air channel in order to pass a atmospheric air through the air-permeable filter 6 to the reference electrode in solid electrolyte tube 1. For this purpose, as is shown in FIGS. 2 and 3, the most preferred embodiment of the first elastic member 7 is an annular elastic member having a concentric groove 17 on the surface of the ring of the annular member and a plurality of apertures 18 provided in the groove 17. By using such an annular elastic member, introduction of air from apertures 18 can be achieved in whatever position the elastic member 7 with such a structure being pressed by means of a second elastic member 12.

It is preferred that the second elastic member 12 is supported, as shown in FIG. 1, by the shoulder of electric insulation member 11 and held so as to press the electrode terminal 4 against the reference electrode, and however another holding means, such as a supporting member to hold it on the inside surface of housing 2 or metallic sleeve 3, may be adopted.

Outside the air passages 5, namely, on the outside peripheral surface of the metallic sleeve 3, is provided a metallic cover 8 for protecting the air passages 5, which is fixed on the metallic sleeve 3 at the neck of the metallic sleeve 3 with rubber grommet 15 plugged therein, or at a part corresponding to the position of electric insulation member 11, on the barrel of the metallic sleeve 3.

The material for the filter 6 should be air-permeable, watertight and heat resistant. For example, Teflon (polytetrafluoroethylene), etc. as disclosed in U.S. Pat. No. 4,116,797 can be used and preferably exhibit an air-permeability of 1–10,000 cc/sec·cm$^2$ at a pressure difference of 0.5 kg/cm$^2$, with a thickness of 0.5 mm.

The fixing of the metallic cover 8 to the metallic sleeve 3 is not to be hermetic, in order to maintain the reference electrode of solid electrolyte 1 in the same level with the atmospheric pressure. Therefore, when the metallic cover 8 is fixed on the metallic sleeve 3, a non-hermetic, but watertight seal may be held by means of caulking, etc., at the neck of the metallic sleeve 3 with a rubber stopper 15 plugged therein and/or at the barrel corresponding to the position of electric insulation member 11, since the filter 6 is held between electric insulation member 11 and rubber stopper 15.

Figure 4:
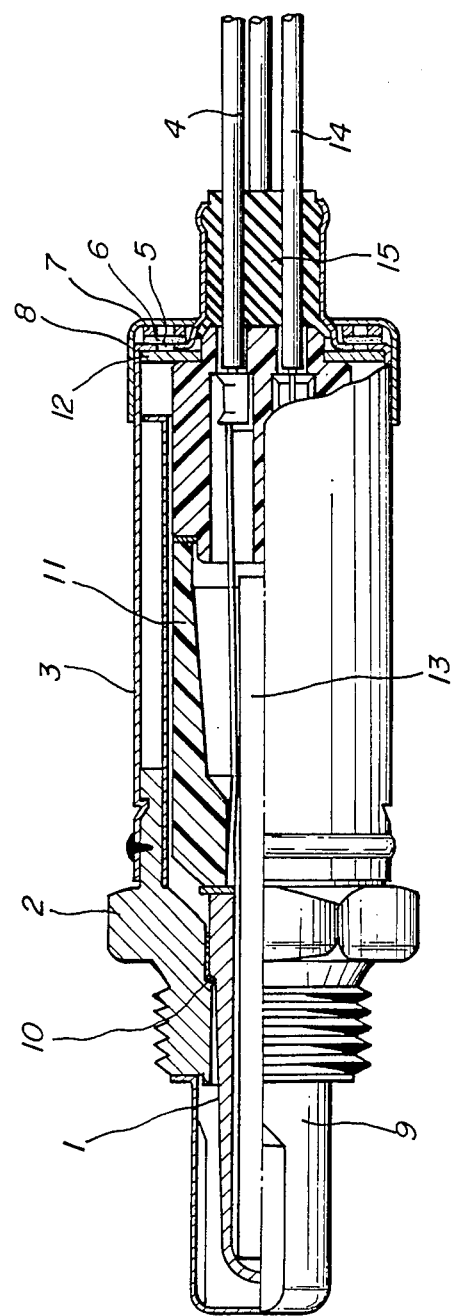
FIG. 4 is a partial sectional view illustrating another embodiment of the present invention.

FIG. 4 shows another embodiment of the present invention, having a structure of a filter and its holding means which are different from those of the oxygen sensor shown in FIG. 1 and described above.

In FIG. 4, the air passages 5 are covered by filter 6 from outside of the metallic sleeve 3. The filter 6 is further pressed against the outside surface of the metallic sleeve 3, by the first elastic member 7 and the metallic cover 8. The metallic cover 8 is fixed at the neck of the metallic sleeve 3 with a rubber grommet 15 plugged therein or at a part corresponding to the position of electric insulation member 11, on the barrel of the metallic sleeve 3.

A similar elastic member 7 for the above embodiment, as illustrated in FIGS. 2 and 3 is used.

If the oxygen sensor is to be mounted in an internal combustion engine, with its measuring electrode side of solid electrolyte tube 1 upward, namely, when fixed in the adverse direction to the ground, it is preferred to fix the metallic cover 8 with a hermetic seal to the metallic sleeve 3 at the part corresponding to the position of electric insulation member 11. Likewise, if it is to be mounted with its measuring electrode side down, namely, with the rubber grommet side up, it is preferred to fix the metallic cover 8 with a hermetic seal to the part corresponding to the rubber grommet 15 on the metallic sleeve 3.

Figure 5:
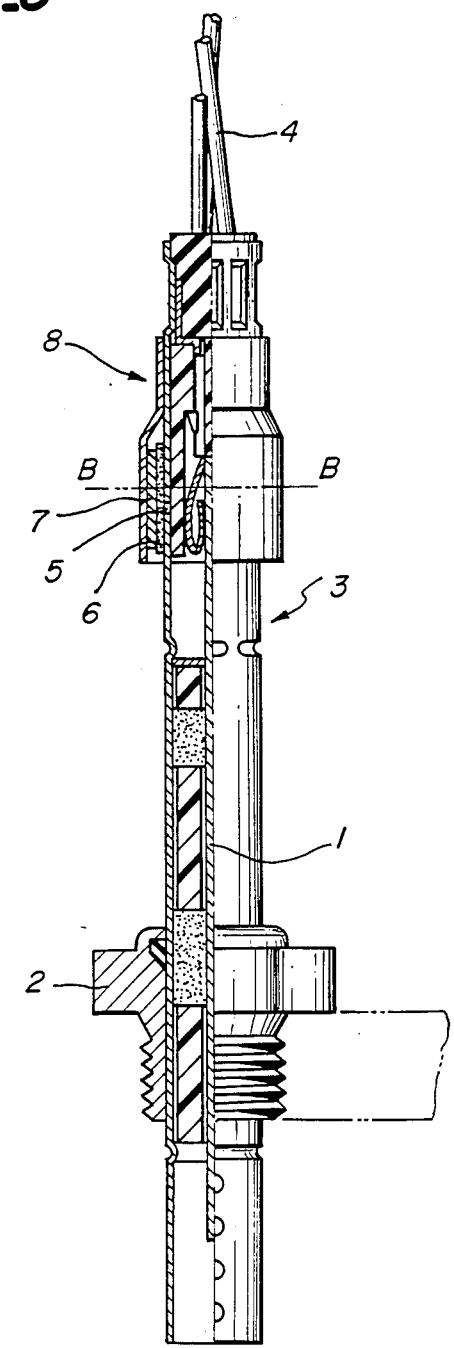
FIG. 5 is a partial sectional view illustrating a further different embodiment of the present invention.

Further, the above embodiment was made in the case where the solid electrolyte is in the form of a tube with a closed end and the metallic cover is provided to cover air passages facing the measuring electrode, and however, the present invention, without being restricted to such a structure, can be applied to an oxygen sensor, such as shown in FIG. 5, which comprises a hollow rectangular solid electrolyte 1 with a closed end and a metallic sleeve 3 enclosing said electrolyte and having air passages 5 on its peripheral wall parallel with the longitudinal axis of the solid electrolyte plate.

Namely, to the upper end portion of metallic sleeve 3 is fixed a metallic cover 8 with a skirt expanded a little and extended downward beyond the position of air passages 5. Then, between the inside surface of the expanded skirt of the metallic cover 8 and the metallic sleeve 3, are laid a filter 6 (composed of the same material as that illustrated with reference to FIG. 4) and an elastic member 7 superimposed outside of the filter.

Figure 6:
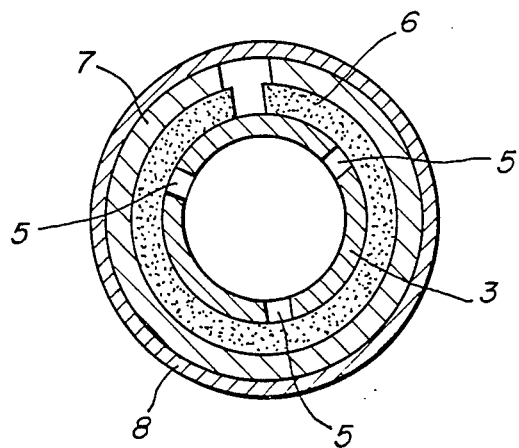
FIG. 6 is a sectional view along the line B—B of FIG. 5.

FIG. 6 shows a sectional view along line B—B of FIG. 5, with all parts inside the metallic sleeve omitted.

Air passages 5 are covered by the filter 6. The filter 6 is pressed against the outside periphery of the metallic sleeve 3, by the first elastic member 7, and by the metallic cover 8.

Figure 7:
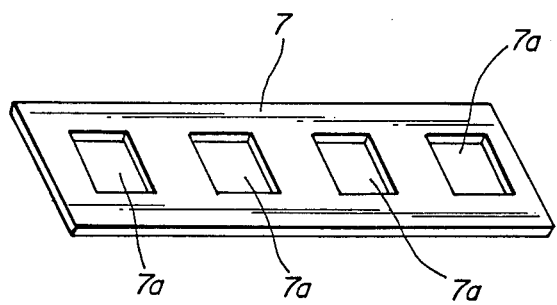
FIG. 7 is a perspective view of an elastic member employed in the embodiment shown in FIGS. 5 and 6.

On the first elastic member 7, a plurality of apertures 7a are formed as shown in FIG. 7. These apertures 7a are formed on an elastic member 7 made of metal, thereby aiming to form a minute clearance between the first elastic member 7 and the metallic cover 8, so that they are combined together watertightly but nonhermetically.

As is clear from the foregoing descriptions, the oxygen sensor according to the present invention is provided with an air-permeable and watertight filter which covers air passages provided on a metallic sleeve, so as to enable the surface of a reference electrode of the solid electrolyte to communicate with the atmosphere as a reference gas and is pressed by an elastic member, so that it has an effect that water is prevented from entering while the oxygen sensor is operating under high temperature conditions, or even when the oxygen sensor is cooled down causing the pressure on the surface of reference electrode to be below the atmospheric pressure after muddy water has adhered to outside surfaces of the oxygen sensor during operation. Moreover, the filter does not separate from air passages which has historically occurred due to a difference in thermal expansion between the filter and the metallic sleeve. Furthermore, the filter can be provided without taking any significant amount of space for lead wires to be inserted.

The present invention may be embodied in other specific forms without departing from the spirit or essential characteristics thereof. The illustrated embodiments should therefore not be considered to be restrictive, rather, the scope of the invention is indicated by the appended claims and all changes which come within the meaning and range of equivalency of the claims are therefore intended to be embraced therein.

What is claimed is:

1. An oxygen sensor comprising a solid electrolyte tube having a closed and an open end, said closed end having an electrode on an inside and an outside surface thereof, a housing supporting said electrolyte tube and isolating the inside surface of the electrolyte tube hermetically from an exhaust gas, said closed end of the tube protruding from the housing toward the exhaust gas, and a metallic sleeve is fixed to said housing, said metallic sleeve enclosing the open end of said solid electrolyte tube and including at least one air passage therein, a filter covering said at least one air passage and a first metallic member for supporting said filter, said first metallic member including a plurality of aperatures therethrough and at least one air groove which communicates with said apertures, whereby said filter is sandwiched between said metallic sleeve and said first metallic member such that each of said at least one passage in the metallic sleeve communicates with said plurality of apertures in said first metallic member through said filter.

2. An oxygen sensor as claimed in claim 1, wherein said first metallic member is provided on an inside surface of said metallic sleeve facing the solid electrolyte tube.

3. An oxygen sensor as claimed in claim 2, wherein a second metallic member is provided to press the first metallic member against the filter.

4. An oxygen sensor as claimed in claim 3, wherein the second metallic member presses against an electric insulation member which is in contact at an end thereof with a rubber grommet through which an electrode terminal is inserted.

5. An oxygen sensor as claimed in claim 1, wherein the first metallic member is provided on an outside surface of said metallic sleeve.

6. An oxygen sensor as claimed in claim 5, wherein a metallic cover is further provided to cover the first metallic member.

* * * * *